United States Patent
Richardson et al.

(10) Patent No.: US 11,124,888 B2
(45) Date of Patent: *Sep. 21, 2021

(54) COPPER DEPOSITION IN WAFER LEVEL PACKAGING OF INTEGRATED CIRCUITS

(71) Applicant: MacDermid Enthone Inc., Waterbury, CT (US)

(72) Inventors: Thomas Richardson, Killingworth, CT (US); Kyle Whitten, Hamden, CT (US); Vincent Paneccasio, Jr., Madison, CT (US); John Commander, Old Saybrook, CT (US); Richard Hurtubise, Clinton, CT (US)

(73) Assignee: MacDermid Enthone Inc., Waterbury, CT (US)

(*) Notice: Subject to any disclaimer, the term of this patent is extended or adjusted under 35 U.S.C. 154(b) by 97 days.

This patent is subject to a terminal disclaimer.

(21) Appl. No.: 16/334,098

(22) PCT Filed: Sep. 20, 2017

(86) PCT No.: PCT/US2017/052449
§ 371 (c)(1),
(2) Date: Mar. 18, 2019

(87) PCT Pub. No.: WO2018/057590
PCT Pub. Date: Mar. 29, 2018

(65) Prior Publication Data
US 2019/0368064 A1  Dec. 5, 2019

Related U.S. Application Data

(60) Provisional application No. 62/398,316, filed on Sep. 22, 2016.

(51) Int. Cl.
| | | |
|---|---|---|
| C25D 3/38 | (2006.01) | |
| C25D 7/12 | (2006.01) | |
| C08G 65/24 | (2006.01) | |
| C08G 65/333 | (2006.01) | |
| C08G 73/06 | (2006.01) | |
| H01L 23/00 | (2006.01) | |

(52) U.S. Cl.
CPC .............. *C25D 3/38* (2013.01); *C08G 65/24* (2013.01); *C08G 65/33317* (2013.01); *C08G 73/0627* (2013.01); *H01L 24/11* (2013.01); *C25D 7/123* (2013.01); *H01L 2224/11462* (2013.01); *H01L 2924/01029* (2013.01); *H01L 2924/3656* (2013.01)

(58) Field of Classification Search
None
See application file for complete search history.

(56) References Cited

U.S. PATENT DOCUMENTS

| | | | | |
|---|---|---|---|---|
| 3,885,913 | A | * | 5/1975 | Redmore ................ C23F 11/04 |
| | | | | 422/12 |
| 4,336,114 | A | | 6/1982 | Mayer |
| 4,555,315 | A | * | 11/1985 | Barbieri .................. C25D 3/38 |
| | | | | 205/296 |
| 6,344,918 | B1 | | 2/2002 | Berneth et al. |
| 8,388,824 | B2 | | 3/2013 | Paneccasio, Jr. et al. |
| 9,028,668 | B2 | | 5/2015 | Isono et al. |
| 10,519,557 | B2 | * | 12/2019 | Paneccasio, Jr. ....... C08L 71/03 |
| 2003/0216025 | A1 | | 11/2003 | Lu et al. |
| 2004/0249177 | A1 | * | 12/2004 | Wang ........................ C25D 3/38 |
| | | | | 549/563 |
| 2010/0126872 | A1 | * | 5/2010 | Paneccasio, Jr. ......................... |
| | | | | H01L 21/76879 |
| | | | | 205/123 |
| 2013/0199935 | A1 | | 8/2013 | Richardson et al. |
| 2016/0076160 | A1 | | 3/2016 | Whitten et al. |
| 2016/0254156 | A1 | | 9/2016 | Richardson et al. |
| 2017/0183791 | A1 | * | 6/2017 | Sun ........................... C25D 3/38 |

FOREIGN PATENT DOCUMENTS

| | | |
|---|---|---|
| CN | 1918327 A | 2/2007 |
| CN | 102362013 A | 2/2012 |
| CN | 108779240 A | 11/2018 |
| JP | 61-041787 | 2/1986 |
| JP | 2012-510179 | 4/2012 |
| JP | 2014/508859 | 4/2014 |
| WO | 2005/066391 A1 | 7/2005 |
| WO | 2010/062822 A2 | 6/2010 |
| WO | 2012/103357 A1 | 8/2012 |
| WO | 2017/139087 A1 | 8/2017 |

* cited by examiner

*Primary Examiner* — Louis J Rufo
(74) *Attorney, Agent, or Firm* — Carmody Torrance Sandak & Hennessey LLP

(57) ABSTRACT

An electrodeposition composition comprising: (a) a source of copper ions; (b) an acid; (c) a suppressor, and (d) a leveler, wherein the leveler comprises a quaternized dipyridyl compound prepared by reacting a dipyridyl compound with a difunctional alkylating agent or a quaternized poly(epihalohydrin). The electrodeposition composition can be used in a process for forming a copper feature over a semiconductor substrate in wafer level packaging to electrodeposit a copper bump or pillar on an underbump structure of a semiconductor assembly.

17 Claims, No Drawings

COPPER DEPOSITION IN WAFER LEVEL PACKAGING OF INTEGRATED CIRCUITS

CROSS REFERENCE TO RELATED APPLICATIONS

The present application claims the benefit of U.S. Provisional Application Ser. No. 62/398,316, filed on Sep. 22, 2016, the subject matter of which is herein incorporated by reference in its entirety.

FIELD OF THE INVENTION

The present invention relates generally to the electrodeposition of copper in the manufacture of electronic circuits and plating bath formulations in forming features in wafer level packaging (WLP) applications.

BACKGROUND OF THE INVENTION

In order to take advantage of the progressively finer and denser architecture of integrated circuits, it is necessary to also provide corresponding ultra-miniaturization of semiconductor packaging. Among the structural requirements for this purpose are increases in the density of input/output transmission leads in an integrated circuit chip.

In flip chip packaging, the leads comprise bumps or pillars on a face of the chip, and more particularly on the side of the chip that faces a substrate, such as a printed circuit board (PCB), to which the circuitry of the chip is connected.

Input and output pads for flip chip circuitry are often provided with solder bumps through which the pads are electrically connected to circuitry external to the chip, such as the circuits of a PCB or another integrated circuit chip. Solder bumps are provided from relatively low melting point base metals and base metal alloys comprising metals such as lead, tin, and bismuth. Alloys of base metals with other electrically conductive metals, such as Sn/Ag alloys are also used.

In the manufacture of the packaged chip, the bumps are provided as globular molten beads on the so-called under bump metal of the pad, and allowed to solidify in place to form the electrical connector through which current is exchanged between the chip and the external circuit. Unless subjected to lateral or vertical constraint during solidification, solder bumps generally assume a spherical form. As a result, the cross-sectional area for current flow at the interface with the under bump metal or pad may depend on the wettability of the under bump structure by the solder bump composition. Absent external constraints on the extent of lateral growth, the height of the bump cannot exceed its lateral dimension, and is diminished relative to the height as wettability of the under bump metal by the molten solder increases. Thus, dimensions of an unconstrained solder bump are determined mainly by the surface tension of the molten solder, the interfacial tension between the solder and the under bump metal, and the extent to which the volume of the solder drop can be controlled in operation of the solder delivery mechanism used in the process.

In an array of solder bumps formed on the face of an integrated circuit chip, these factors may limit the fineness of the pitch, i.e., the distances between the centers of immediately neighboring bumps in the array.

In order to achieve a finer pitch, attempts have been made to substitute copper bumps or pillars for the solder by electrodeposition onto the under bump metal. However, it can be difficult to control the electrodeposition process to provide a copper pillar having the desired configuration. While the shape of the main body of the pillar can be determined by forming it within the confines of a cavity having sidewalls formed from a dielectric material, the configuration of the distal end of the pillar may still be unsatisfactory, e.g., excessively domed, excessively dished, or irregular.

By comparison with the provision of solder bumps, manufacturing of copper pillars can suffer a further disadvantage in productivity, and in the effect of productivity on manufacturing cost. While a drop of molten solder can be delivered almost instantaneously once a delivery head is brought into registry with the under bump metal, the rate of electrodeposition of a copper pillar is limited by the maximum current density that can be achieved in the electrodeposition circuit. In commercial practice, the current density is limited by various configuration problems, including the problems of doming, dishing, and irregular configuration at the distal end of a copper pillar, which are aggravated if the current density rises above a limiting value, for example, about 40 $A/dm^2$, depending on the application, corresponding to a vertical growth rate of no greater than about 7 µm/min.

Although copper bumps and pillars have substantial advantages over tin/lead solder bumps, a small bead of solder is still used in the manufacturing process to bond the end of the bump or pillar to external circuitry such as the circuit traces of a PCB. However, to assure proper bonding of copper to the solder, and to prevent formation of Kirkendall voids (i.e., voids formed at the boundary interface in various kinds of alloys to bonding) at the copper/solder interface that may result from migration of copper into the solder phase, it has been necessary to provide a nickel cap on the distal end of the bump or pillar as a barrier between the copper phase and the solder phase, thus adding to the expense and complication of the manufacturing process.

SUMMARY OF THE INVENTION

Described herein are improved compositions and processes for electrodeposition of wafer level packaging (WLP) features. Particularly effective for this purpose is a process in which a feature such as a bump, pillar, or megabump is deposited from a plating solution that comprises a source of copper ions, an acid, a leveler, a suppressor, and an accelerator.

The process described herein is effective for forming WLP features on semiconductor substrates for interconnection of an electronic circuit of a semiconductor device with a circuit external to the device. This includes, for example, features having diameters as small as about 1 µm or as large as about 240 µm, and heights as small as about 2 µm and as large as about 300 µm; with aspect ratios between about 1:1 and about 2:1, and up to about 10:1 or even up to about 20:1. In one embodiment, current is supplied to an electrolytic solution in contact with a cathode comprising a WLP structure such as an under bump structure on a semiconductor assembly, wherein the electrolytic solution comprises a source of copper ions, an acid, a leveler, and a suppressor, thereby electrodepositing a copper bump or pillar on the under bump structure.

DESCRIPTION OF PREFERRED EMBODIMENTS

In various preferred embodiments of the invention, as described herein, a copper bump or pillar having a suitable distal configuration is deposited at a relatively high rate of vertical growth. By "suitable distal configuration" what is meant is that the copper bump or pillar is not unduly domed, unduly dished, or irregular in shape. The rate of growth of bumps and pillars having suitable distal configurations compares favorably with the rate that is achieved using electrodeposition baths that do not involve the composition and process described herein.

The electrolytic plating bath generally comprises:
a) a source of copper ions;
b) an acid component;
c) a suppressor;
d) a leveler, wherein the leveler comprises a quaternized dipyridyl compound or a quaternized poly(epihalohydrin), and
e) an accelerator.

The source of copper ions in the electrolytic plating bath may be any of a variety of water-soluble copper salts, including, for example, copper sulfate or a copper salt of an alkanesulfonic acid such as methane sulfonic acid or ethane sulfonic acid.

The acid component is preferably sulfuric acid or an alkane sulfonic acid, such as methane sulfonic acid or ethane sulfonic acid, most preferably methane sulfonic acid. Preferably, the conjugate base of the acid is the same as the counteranion of the copper salt, but mixtures can also be effective, including, for example, copper sulfate and methane sulfonic acid, or copper methane sulfonate and sulfuric acid.

The concentration of copper and acid may vary over wide limits, and may be for example, from about 20 to about 100 g/L copper and from about 40 to about 300 g/L acid. In many embodiments, the copper ion concentration can be greater than about 30 g/L, 40 g/L, and even up to on the order of 60 or 80, such as from about 25 to about 100 g/L copper (50 g/L copper corresponds to 200 g/L $CuSO_4.5H_2O$ Cu sulfate pentahydrate). The acid concentration in these systems is on the order of about 50 to about 300 g/L, preferably about 80 to about 220 g/L in some embodiments.

Chloride ions may also be used in the bath at a level up to 100 mg/L, preferably within the range of about 10 to 90 mg/L, more preferably in the range of 30 to 80 mg/L. The addition of chloride ions at these concentration ranges enhances the function of other bath additives. These other bath additives include accelerators, suppressors, and levelers. Table 1 describes various make-up compositions with varying copper and acid concentrations:

TABLE 1

Sample bath make-up compositions

| | $Cu^{2+}$ (g/L) | Acid (g/L) | Cl (mg/L) |
|---|---|---|---|
| 1 | 32.0 | 180 $H_2SO_4$ | 50 |
| 2 | 40.0 | 140 $H_2SO_4$ | 50 |
| 3 | 50.0 | 100 $H_2SO_4$ | 50 |
| 4 | 55.0 | 150 $H_2SO_4$ | 50-80 |
| 5 | 62.5 | 100 $H_2SO_4$ | 50 |
| 6* | 80.0 | 100 MSA | 50 |
| 7 | 40.0 | 100 MSA | 50 |

*$Cu^{2+}$ in 5 is from CuMSA; $Cu^{2+}$ for others is from $CuSO_4$.

The electrodeposition composition contains a leveler compound in a suitable concentration, such as between about 1.0 and about 100 mg/L, more preferably, between about 5.0 and about 50 mg/L.

Among the levelers useful in the novel process described herein are polymers and oligomers formed by the reaction of a dipyridyl compound and a difunctional alkylating agent and quaternized poly(epihalohydrin) polymers.

A wide range of such quaternized dipyridyl reaction products are described in U.S. Pat. No. 8,388,824 to Paneccasio et al., the subject matter of which is herein incorporated by reference in its entirety.

Dipyridyls that may be quaternized to prepare the levelers of for the electrodeposition of WLP features such as bumps and pillars have the general structure (I):

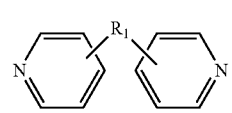

Structure (I)

wherein $R_1$ is a moiety that connects the pyridine rings. In Structure (I), each line from $R_1$ to one of the pyridine rings denotes a bond between an atom in the $R_1$ moiety and one of the five carbon atoms of the pyridine ring. In some embodiments, $R_1$ denotes a single bond wherein one carbon atom from one of the pyridine rings is directly bonded to one carbon atom from the other pyridine ring.

In certain advantageous embodiments, the $R_1$ connection moiety may be an alkylene chain, and the dipyridyl may have the general structure (Ia):

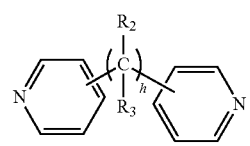

Structur (Ia)

wherein h is an integer from 0 to 6, and $R_2$ and $R_3$ are each independently selected from hydrogen and short alkyl chains having from 1 to about 3 carbon atoms. In Structure (a), each line from a carbon in the alkylene chain to one of the pyridine rings denotes a bond between a carbon atom in the alkylene chain and one of the five carbon atoms of the pyridine ring. In embodiments wherein h is 0, the connecting moiety is a single bond, and one carbon atom from one of the pyridine rings is directly bonded to one carbon atom from the other pyridine ring.

In some embodiments, the $R_1$ connecting moiety may contain a carbonyl, and the dipyridyl may have the general structure (Ib):

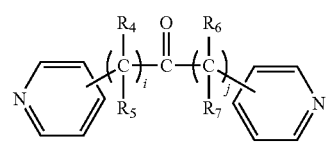

Structure (Ib)

wherein i and j are integers from 0 to 6, and $R_4$, $R_5$, $R_6$, and $R_7$ are each independently selected from hydrogen and short alkyl chains having from 1 to about 3 carbon atoms. In Structure (Ib), each line from a carbon in the connecting moiety to one of the pyridine rings denotes a bond between the carbon atom in the connecting moiety and one of the five carbon atoms of the pyridine ring. In embodiments wherein i and j are both 0, the carbon atom of the carbonyl is directly bonded to one carbon atom in each of the pyridine rings.

Two compounds in the general class of dipyridyls of structure (Ib), in which i and j are both 0, are 2,2'-dipyridyl ketone and 4,4'-dipyridyl ketone, having the structures shown below:

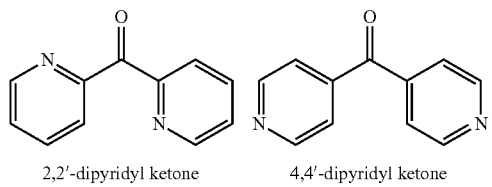

2,2'-dipyridyl ketone        4,4'-dipyridyl ketone

In some embodiments, the $R_1$ connecting moiety may contain an amine, and the dipyridyl may have the general structure (Ic):

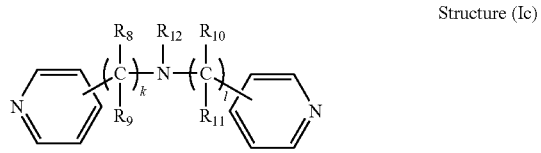

Structure (Ic)

wherein k and l are integers from 0 to 6, and $R_8$, $R_9$, $R_{10}$, $R_{11}$, and $R_{12}$ are each independently selected from hydrogen and short alkyl chains having from 1 to about 3 carbon atoms. In Structure (Ic), each line from a carbon in the connecting moiety to one of the pyridine rings denotes a bond between the carbon atom in the connecting moiety and one of the five carbon atoms of the pyridine ring. In embodiments wherein k and l are both 0, the nitrogen is directly bonded to one carbon atom in each of the pyridine rings.

One compound in the general class of dipyridyls of structure (Ic), in which k and l are both 0 and $R_{12}$ is hydrogen, is dipyridin-4-ylamine having the structure shown below:

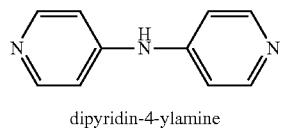 [SMILES: c1cc(Nc2ccncc2)ccn1]

dipyridin-4-ylamine

In some embodiments, the $R_1$ connecting moiety comprises another pyridine. Such a structure is actually a terpyridine having the general structure (Id):

Structure (Id)

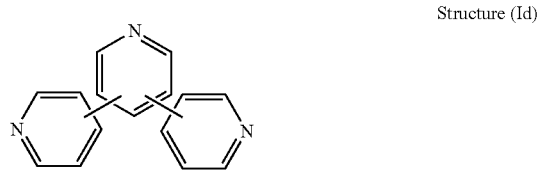

In structure (Id), each line from each pyridine ring denotes a bond between one carbon on one ring and another carbon on another ring.

One such compound in the general class compounds of structure (Id) is terpyridine having the structure:

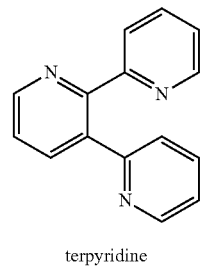 [SMILES: c1ccc(-c2cccnc2-c2ccccn2)nc1]

terpyridine

Preferably, the dipyridyl is chosen from the general class of dipyridyls of general structure (Ia), and further in which R2 and R3 are each hydrogen. These dipyridyls have the general structure (IIa):

Structure (IIa)

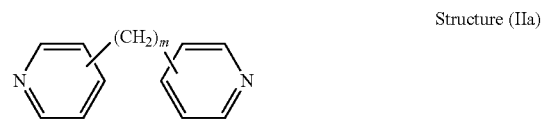

wherein m is an integer from 0 to 6. In Structure (IIa), each line from a carbon atom in the alkylene chain to one of the pyridine rings denotes a bond between a carbon atom in the alkylene chain and one of the five carbon atoms of the pyridine ring. In embodiments wherein m is 0, the connecting moiety is a single bond, and one carbon atom from one of the pyridine rings is directly bonded to one carbon atom from the other pyridine ring.

Dipyridyls of the above general structure (IIa) include 2,2'-dipyridyl compounds, 3,3'-dipyridyl compounds, and 4,4'-dipyridyl compounds, as shown in the following structures (IIb) through (IId), respectively:

Structure (IIb)

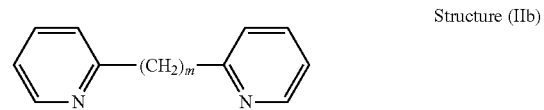

Structure (IIc)

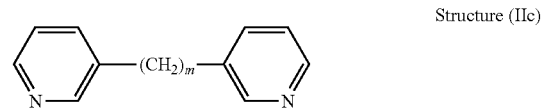

Structure (IId)

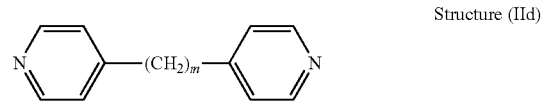

wherein m is an integer from 0 to 6. When m is 0, the two pyridine rings are directly bonded to each other through a single bond.

2,2'-dipyridyl compounds include 2,2'-dipyridyl, 2,2'-ethylenedipyridine (1,2-Bis(2-pyridyl)ethane), Bis(2-pyridyl) methane, 1,3-Bis(2-pyridyl)propane, 1,4-Bis(2-pyridyl)butane, 1,5-Bis(2-pyridyl)pentane, and 1,6-Bis(2-pyridyl) hexane.

3,3'-dipyridyl compounds include 3,3'-dipyridyl, 3,3'-ethylenedipyridine (1,2-Bis(3-pyridyl)ethane), Bis(3-pyridyl) methane, 1,3-Bis(3-pyridyl)propane, 1,4-Bis(3-pyridyl)butane, 1,5-Bis(3-pyridyl)pentane, and 1,6-Bis(3-pyridyl) hexane.

4,4'-dipyridyl compounds include, for example, 4,4'-dipyridyl, 4,4'-ethylenedipyridine (1,2-Bis(4-pyridyl)ethane), Bis(4-pyridyl)methane, 1,3-Bis(4-pyridyl)propane, 1,4-Bis(4-pyridyl)butane, 1,5-Bis(4-pyridyl)pentane, and 1,6-Bis(4-pyridyl)hexane.

Of these dipyridyl compounds, 4,4'-dipyridyl compounds are preferred since compounds based on 4,4'-dipyridyl have been found to be particularly advantageous levelers in terms of achieving low impurity inclusion and underplate and overplate reduction. Among the preferred dipyridyls are 4,4'-dipyridyls having the structure (IIe) and 4,4'-ethylenedipyridine, having structure (IIf).

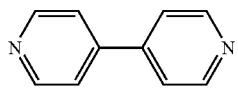

Structure (IIe)

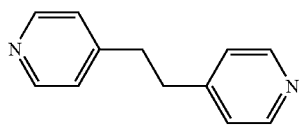

Structure (IIf)

The leveler compounds used in some preferred electrodeposition compositions described herein are quaternized dipyridyl compounds, typically prepared by alkylating at least one and preferably both of the nitrogen atoms. Alkylation occurs by reacting the dipyridyl compounds with an alkylating agent. In some embodiments, the alkylating agent may be of a type particularly suitable for forming polymers (see alkylating agents having structures (IIIb) and (IIIc) below). Alkylating agents that react with the dipyridyl compounds and generally form polymeric levelers may have the general structure (IIIb):

$$Y-(CH_2)_p-B-(CH_2)_q-Z \qquad \text{Structure (IIIb)}$$

wherein

B may be selected from among:

a single bond, an oxygen atom (—O—), a methenyl hydroxide

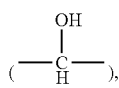

a carbonyl

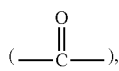

an amino

an imino

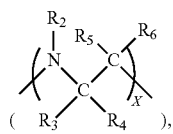

a sulfur atom (—S—), a sulfoxide

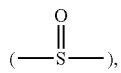

a phenylene

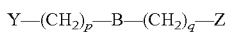

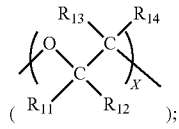

and a glycol and p and q may be the same or different, are integers between 0 and 6, preferably from 0 to 2, wherein at least one of p and q is at least 1;

X is an integer from one to about four, preferably one or two; and

Y and Z are leaving groups. The leaving group may be selected from among, for example, chloride, bromide, iodide, tosyl, triflate, sulfonate, mesylate, methosulfate, fluorosulfonate, methyl tosylate, brosylate, or nosylate.

In each B group above, the single line emanating from the functional moiety denotes a bond between an atom in the B moiety, e.g., oxygen, nitrogen, or carbon, and a carbon of the —$(CH_2)_p$— and —$(CH_2)_q$-alkylene groups. Additionally, the R1 through R14 groups in denoted in the B moieties of Structure (IIIb) are independently hydrogen; substituted or unsubstituted alkyl having from one to six carbon atoms, preferably one to three carbon atoms; substituted or unsubstituted alkylene having from one to six carbon atoms, preferably from one to three carbon atoms; or substituted or unsubstituted aryl. The alkyl may be substituted with one or more of the following substituents: halogen, heterocyclo, alkoxy, alkenoxy, alkynoxy, aryloxy, hydroxy, protected hydroxy, hydroxycarbonyl, keto, acyl, acyloxy, nitro, amino, amido, nitro, phosphono, cyano, thiol, ketals, acetals, esters and ethers. In general, the various R groups are hydrogen or unsubstituted alkyl, and even more preferably, the R groups are hydrogen.

Preferably, B is selected from the group consisting of:
an oxygen atom (—O—),
a methenyl hydroxide $$\left(-\underset{H}{\overset{OH}{\underset{|}{C}}}-\right),$$

a carbonyl $$\left(-\overset{O}{\underset{\|}{C}}-\right),$$

a phenylene group (—⌬—), an ethylene glycol group $$\left(\diagdown_O\diagdown\underset{H_2}{\overset{H_2}{C}}\diagup_C\diagdown_O\diagup\right),$$

and
a propylene glycol group $$\left(\diagdown_O\diagdown\underset{}{\overset{H_2}{C}}\diagdown\underset{CH_3}{\overset{H}{C}}\diagup_O\diagup\right).$$

More preferably, B is selected from the group consisting of:
an oxygen atom (—O—),
a methenyl hydroxide $$\left(-\underset{H}{\overset{OH}{\underset{|}{C}}}-\right),$$

a carbonyl $$\left(-\overset{O}{\underset{\|}{C}}-\right),$$

a phenylene group (—⌬—), and
an ethylene glycol group $$\left(\diagdown_O\diagdown\underset{H_2}{\overset{H_2}{C}}\diagup_C\diagdown_O\diagup\right).$$

Preferably, the structure —(CH$_2$)p-B—(CH$_2$)q- is aliphatic. It is also preferred that, in the alkylating agents of Structure (IIb), p and q are both one or are both two, and Y and Z are both chloride.

Another class of alkylating agents that may form a polymeric leveler when reacted with the dipyridyl compounds includes an oxirane ring and has the general structure (Ic):

Structure (IIIc)

$$Y-(CH_2)_o-\overset{R_{13}}{\underset{|}{C}}-\overset{O}{\overset{/\backslash}{C}}-R_{11}$$
$$\phantom{Y-(CH_2)_o-C-C}R_{12}$$

wherein
R$_{11}$, R$_{12}$, and R$_{13}$ are hydrogen or substituted or unsubstituted alkyl having from one to six carbon atoms, preferably from one to three carbon atoms;
o is an integer between one and six, preferably one or two; and
Y is a leaving group. The leaving group may be selected from among, for example, chloride, bromide, iodide, tosyl, triflate, sulfonate, mesylate, methosulfate, fluorosulfonate, methyl tosylate, brosylate, or nosylate.

Preferably, R$_{11}$, R$_{12}$, and R$_{13}$ are hydrogen and the alkylating agent has the following general structure:

$$Y-(CH_2)_o-\underset{H}{\overset{}{\underset{|}{C}}}-\overset{O}{\overset{/\backslash}{C}}H_2$$

wherein o and Y are as defined in connection with Structure (IIIc).

Preferably, o is one, Y is chloride, and the alkylating agent of general Structure (IIIc) is epichlorohydrin.

The reaction product causes the leaving group to form an anion in the reaction mixture. Since chloride is commonly added to electrolytic copper plating compositions, Y and Z are preferably chloride. While other leaving groups may be used to form the leveling compounds suitable for use in the process described herein, they are less preferred since they may adversely affect the electrolytic plating composition. Leveling agents that are charge balanced with, for example, bromide or iodide, are preferably ion exchanged with chloride prior to adding the leveling compound to the electrolytic copper plating compositions used in the process.

A wide variety of leveler compounds may be prepared from the reaction of the dipyridyl compounds having the general structures (I), (Ia), (Ib), (Ic), (Id), (IIa), (Ib), (IIc), (IId), (IIe), and (IIf) and the alkylating agents having the general structures (IIIb), and (IIc). Reactions to prepare the leveler compounds may occur according to the conditions described in U.S. Pat. No. 5,616,317 to Nagose et al., the subject matter of which is herein incorporated by reference in its entirety. In the reaction, the leaving groups are displaced when the nitrogen atoms on the pyridyl rings react with and bond to the methylene groups in the dihalogen compound. Preferably, the reaction occurs in a compatible organic solvent, preferably having a high boiling point, such as ethylene glycol or propylene glycol.

In preparing the polymeric or oligomeric dipyridyl-based levelers useful in the compositions and processes described herein, reaction conditions, i.e., temperature, concentration, and the alkylating agent are selected such that the dipyridyl compound and alkylating agent polymerize, wherein the repeat units of the polymer comprise one moiety derived from the dipyridyl compound and one moiety derived from the alkylating agent. In some embodiments, the dipyridyl compound has the structure (IIa) and the alkylating agent has the general structure depicted above in Structure (IIIb). In some embodiments, therefore, the leveler compound is a polymer comprising the following general structure (IV):

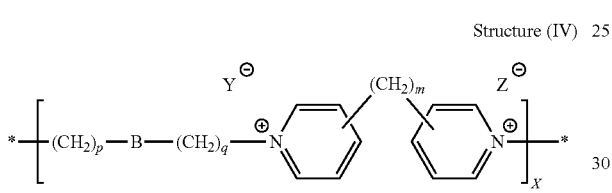

Structure (IV)

wherein B, m, p, q, Y, and Z are as defined with regard to structures (IIa) and (IIIb) and X is an integer that is at least 2. Preferably, X ranges from 2 to about 100, such as from about 2 to about 50, from about 2 to about 25, and even more preferably from about 4 to about 20.

In some preferred embodiments, the leveler compound is a reaction product of 4,4'-dipyridyl of structure (IIf) and an alkylating agent of structure (IIIb). Reaction conditions, i.e., temperatures, relative concentrations, and choice of alkylating agent may be selected such that 4,4'-ethylenedipyridine and the alkylating agent polymerize, wherein the repeat units of the polymer comprise one moiety derived from 4,4'-ethylenedipyridine and one moiety derived from the alkylating agent. In some embodiments, therefore, the leveler compound is a polymer comprising the following general structure (VII):

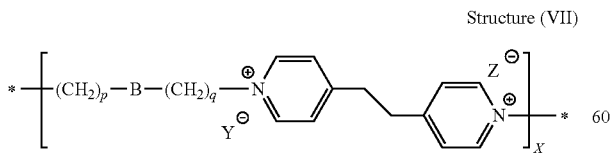

Structure (VII)

wherein B, p, q, Y, and Z are as defined with regard to structure (IIIb) and X is an integer of at least 2, preferably from 2 to 100, such as from 2 to 50, and more preferred from 3 to about 20.

Particularly preferred levelers include:

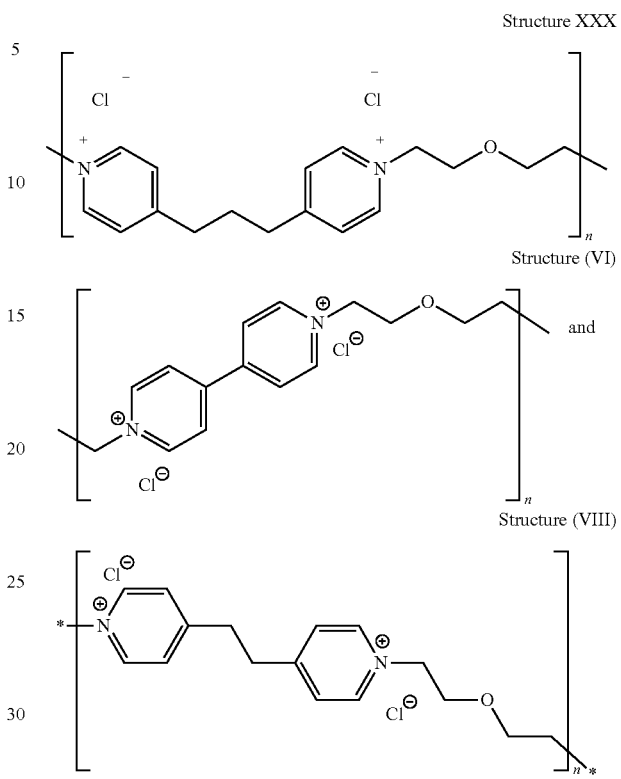

Structure XXX

Structure (VI)

Structure (VIII)

where the value of n is preferably between about 5 and about 20, such as between 6 and 9 in a low molecular weight embodiment or between 10 and 15 in a higher molecular weight embodiment, and/or is such that the polymer or oligomer has a number average molecular weight between about 1000 and about 5000.

Other specific embodiments of leveler structure (VII) include structure

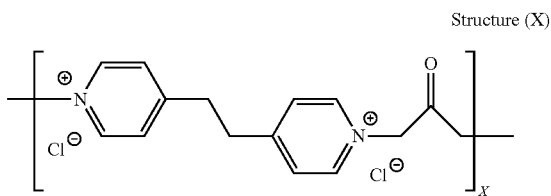

Structure (X)

wherein X is an integer of at least 2, preferably from 2 to 100, such as from 2 to 50, and more preferred from 3 to about 20.

Yet another embodiment of the leveler of structure (VII) is the leveler of structure (XI):

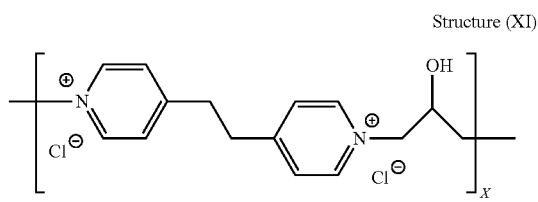

Structure (XI)

wherein X is an integer of at least 2, preferably from 2 to 100, such as from 2 to 50, and more preferred from 3 to about 20, still more preferably between about 5 and about 20, most preferably between about 10 and about 15.

In each of the polymeric structures depicted above, the value of n or X most preferably ranges from 10 to 15 and the number average molecular weight ranges from about 2,500 to about 4,000, more preferably between about 2,800 and about 3,000, most preferably between about 3,000 and about 3,600.

Another class of dipyridyl-derived levelers that may be used in the novel process for electrodeposition of bumps and pillars comprises a compound having the structure of the reaction product of N,N'-tetraalkylthiourea with an intermediate produced by reaction of a dipyridyl with a difunctional alkylating agent.

A particularly preferred leveler of this class can be prepared, for example, but the reaction of compound C with an intermediate oligomer or polymer that is produced by reaction of dipyridyl (B) with an aralkylene difunctional alkylating agent (A)

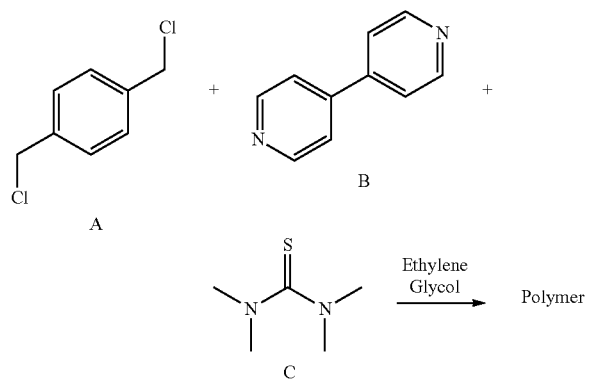

More generically, reactant A corresponds to the structure:

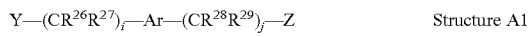

Y—(CR$^{26}$R$^{27}$)$_i$—Ar—(CR$^{28}$R$^{29}$)$_j$—Z     Structure A1 wherein each of Y and Z is a leaving group independently selected from the group consisting of chloride, bromide, iodide, tosyl, triflate, sulfonate, mesylate, methosulfate, fluorosulfonate, methyl tosylate, and brosylate, Ar is an bivalent aryl residue derived, e.g., from benzene, toluene, xylene, naphthalene, etc., each of i and j is an integer between 1 and 12, inclusive, and each of R$^{26}$, R$^{27}$, R$^{28}$, and R$^{29}$ is independently selected from hydrogen and lower alkyls having 1 to 4 carbon atoms. Exemplary compounds that can constitute reactant A are p-di(chloromethyl)benzene, 1,4-bis(2-chloroethyl)benzene, m-di(chloromethyl)benzene, and o-di(chloromethyl)benzene. Alternatively, A can also be described by structure (I).

Reactant B is optionally unsubstituted dipyridyl or dipyridyl that is mono- di-, or tri-substituted with any of various ring substituents, including, e.g., alkyl, aryl, aralkyl, hydoxy, alkoxy, aryloxy, cyano, amido, or carboxyl (i.e., hydroxycarbonyl). Exemplary compounds that can constitute Reactant B include dipyridyl, ethane, propane, or butane, and any of the di(tert-amine)s described by structure (II). Reactant C is preferably a compound that will react with the alkylating agent at the leaving group site, but will not propagate the polymeric reaction. Examples include pyridine, thiourea, and N,N,N',N'-tetralkylthiourea. Alkyl substituents on the urea nitrogen are preferably selected from lower alkyl having 1 to 4 carbon atoms.

In preparation of the dipyridyl-based leveler, the dipyridyl compound B and the difunctional reactant A, both A and B are dissolved in a solvent medium, e.g., ethylene glycol, and reacted in the solvent medium, preferably at a temperature between about 120° C. and about 180° C. Reactant A is preferably present in an initial concentration between about 150 and about 200 g/L, more preferably between about 170 and about 180 g/L. Reactant B is preferably present in an initial concentration between about 50 and about 200 g/L, more preferably between about 70 and about 100 g/L, and molar ratio of Reactant A to Reactant B is preferably between about 3:1 and about 2:3, more preferably between about 1:1 and about 2:1. The reaction generates a salt comprising polymer or oligomer comprising a cation that comprises quaternized dipyridinium repeating units and repeating units comprising the residue of reactant A, and anions derived from the leaving groups Y and Z. The intermediate reaction mixture produced by reaction of reactants A and B is cooled to a temperature of preferably less than about 80° C., after which reactant C is added. The solution is then heated again to a temperature between about 120° C. and about 180° C. to react with the A+B adduct and yield a reaction solution comprising the leveler compound.

Alternatively, reactant A can initially be reacted with reactant C to produce an adduct which is reacted with reactant B to produce the leveler. In this case again the intermediate reaction product is cooled to a temperature preferably below 80° C. before reactant B is added, and the resulting mixture is heated back to a temperature between about 120° and about 180° C. to complete the reaction. According to a still further alternative, reactants A, B and C can all be introduced into the reaction medium and simultaneously reacted to produce a solution comprising the leveler product. Weight average molecular weight of the thiourea-based levelers is typically in the range between about 1000 and about 5000. Where reactant C is N,N,N',N'-tetramethylthiourea, the weight average molecular weight may preferably range from about 300 to about 3000.

Regardless of the exact sequence in which the reactants are combined, a leveler compound produced from p-di(chloromethyl)benzene, dipyridyl and N,N'-tetramethylthiourea has the general structure:

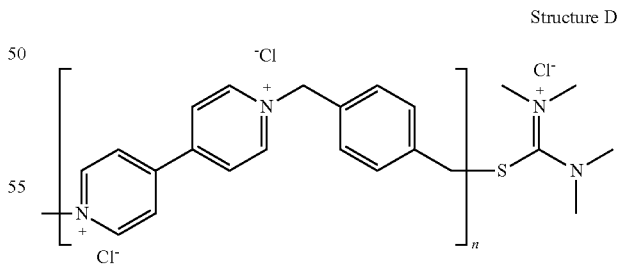

Structure D

More generically, the levelers based on dipyridyl correspond to the above formula except that the substituent on the nitrogens of the thiourea residue may independently be selected from the group consisting of hydrogen and C$_1$ to C$_4$ alkyl and the dipyridyl residue and phenylene ring may each bear one or more of the ring substituents listed above. By way of further example, leveler compounds of the separate class may correspond to the structure:

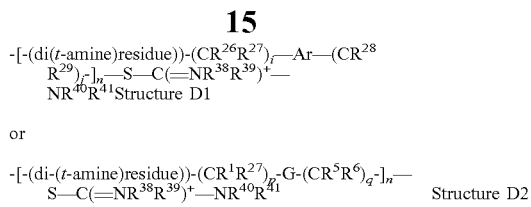Structure D1 or

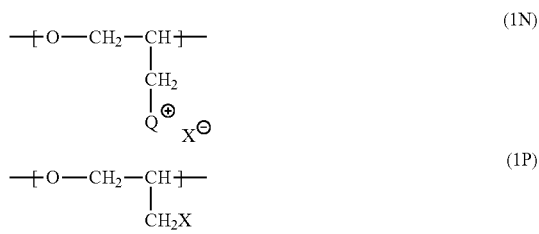Structure D2 where each of $R^{40}$ and $R^{41}$ is independently selected from the group consisting of hydrogen and $C_1$ to $C_4$ alkyl, each of i, j, p, q, $R^1$, $R^2$, $R^5$, $R^6$, $R^{26}$, $R^{27}$, $R^{28}$, $R^{29}$, Ar and G is as defined above, and the di(t-amine) residue is derived, e.g., from any of the dipyridyl or other di-(t-amine) compounds listed above. When prepared from reactants A, B and C as described above, the polymeric leveler may typically comprise a mixture of polymers, oligomers and non-polymeric species.

Also useful as levelers in the electrodeposition of copper bumps, pillars, and other WLP features are quaternized poly(epihalohydrin) polymers as described in copending U.S. provisional application Ser. No. 62/294,643, the subject matter of which is herein incorporated by reference its entirety. In the referenced application, such polymers are referred to by the acronym QPECH.

QPECH polymers that may be used in the electrodeposition composition of this invention may typically comprise n repeating units corresponding to structure 1N and p repeating units corresponding to structure 1P:

$$\begin{array}{c} \text{—}\mathopen{\lgroup} O\text{—}CH_2\text{—}CH\mathclose{\rgroup}\text{—} \\ | \\ CH_2 \\ | \\ Q^{\oplus} \;\; X^{\ominus} \end{array} \quad (1N)$$

$$\begin{array}{c} \text{—}\mathopen{\lgroup} O\text{—}CH_2\text{—}CH\mathclose{\rgroup}\text{—} \\ | \\ CH_2X \end{array} \quad (1P)$$

wherein Q has a structure corresponding to that which may be obtained by reacting a pendent methylene halide group of poly(epihalohydrin) with a tertiary amine selected from the group consisting of: (i) $NR^aR^bR^c$ wherein each of $R^a$, $R^b$ and $R^c$ is independently selected from the group consisting of substituted or unsubstituted alkyl, alicyclic, aralkyl, substituted or unsubstituted alkenyl, substituted or unsubstituted alkynyl, aryl and heterocyclic; (ii) an N-substituted and optionally further substituted heteroalicyclic amine wherein the N-substituent is selected from the group consisting of substituted or unsubstituted alkyl, alicyclic, aralkyl, aryl, and heterocyclic; and (iii) a substituted or unsubstituted nitrogen-containing heteroaryl compound; n is an integer between 3 and 35, p is an integer between 0 and 25; X is a halo substituent; and X is a monovalent anion, ordinarily a halide ion. Where any of $R^a$, $R^b$ and $R^c$ is substituted, the substituent preferably does not comprise an amino group.

Examples of suitable QPECH polymers include, but are not limited to:

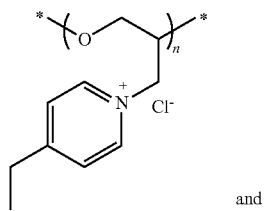

and

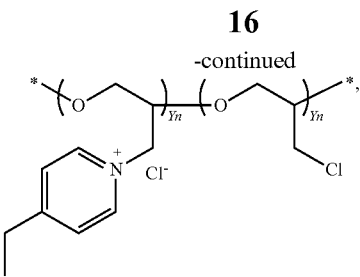

where X is between about 0.3 and 0.7.

The structure and properties of the quaternized poly (epichlorohydrin) are compatible with other components of the electrolytic composition, especially with respect to solubility in the overall composition. Compatibility is a function of various structural parameters, including the extent of quaternization, the presence or absence of repeating units other than 1N and 1P, and molecular weight. By selection of, for example, the molecular weight of the core PECH, the amine for the quaternization reaction, the extent of quaternization, the optional use of co-monomers in polymerizing epihalohydrin, the identity of any co-monomers, and fraction of co-monomers, the composition can be tailored to assure compatibility while imparting the properties that may be optimal for a particular application. Preferably Q in structures I, 1P, and 1N corresponds to structure 2A, 2B, or 2C:

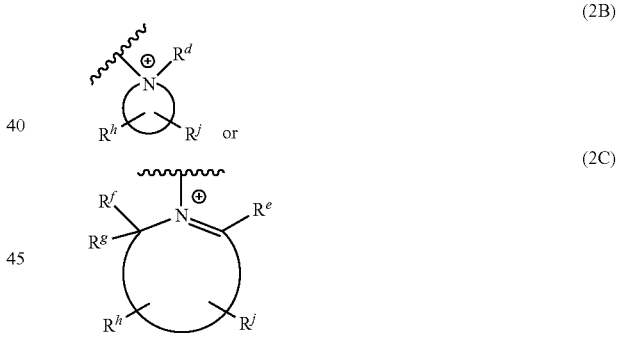

wherein: (i) structure 2B is an N-substituted heterocyclic moiety; (ii) structure 2C is a heterocyclic moiety; (iii) each of $R^a$, $R^b$, $R^c$ and $R^d$ is independently selected from the group consisting of substituted or unsubstituted alkyl, substituted or unsubstituted alkenyl, substituted or unsubstituted alkynyl, substituted or unsubstituted aralkyl, substituted or unsubstituted alicyclic, substituted or unsubstituted aryl, and substituted or unsubstituted heterocyclic; and (iv) each of $R^e$, $R^f$, $R^g$, $R^h$ and $R^j$ is independently selected from the group consisting of hydrogen, substituted or unsubstituted alkyl, substituted or unsubstituted alkenyl, substituted or unsubstituted alkynyl, substituted or unsubstituted aralkyl, substituted or unsubstituted alicyclic, substituted or unsubstituted aryl, and substituted or unsubstituted heterocyclic. Where any of $R^a$ to $R^j$ is substituted, the substituent preferably does not comprise an amino group.

In preferred embodiments of the electrodeposition composition used in the electrodeposition process described herein, Q in structure I corresponds to that which may be obtained by reacting a pendent methylene halide group of poly(epihalohydrin) with a tertiary amine selected from the group consisting of N-methylmorpholine, 1-methylimidazole, 1-benzylimidazole, 2-imidazoline, 3-imidazoline, and $NR^aR^bR^c$ wherein one of $R^a$, $R^b$ and $R^c$ is selected from the group consisting of unsubstituted alkyl having at least three carbon atoms, hydroxyalkyl, dihydroxyalkyl, benzyl, hydroxyphenylmethyl and dihydroxyphenylmethyl, and each of the others of $R^a$, $R^b$ and $R^c$ is independently selected from lower alkyl having between 1 and 3 carbon atoms.

Preferably, Q corresponds to the structure which may be obtained from reacting a pendent methylene halide group with a tertiary amine selected from the group consisting of 3-hydroxypropyldimethylamine, n-butyldimethylamine, di(3-hydroxypropyl)methylamine, 2,3-dihydroxypropyldimethylamine, 3-hydroxypropyldiethylamine, 2-hydroxypropyldimethylamine, 4-hydroxybutyldimethylamine, 2-hydroxyethyldimethylamine, n-propyldimethylamine, 2-hydroxyethoxyethyldimethylamine, di(2-hydroxyethyl) methylamine, benzyldimethylamine, and 4-hydroxybenzyldimethyleamine, 4-methylpyridine, 3-ethylpyridine, 4-propylpyridine, 4-tertbutylpyridine, 4-cyanopyridine, 4-isopropylpyridine, 4-methoxypyridine, 3,4-lutidine, 3-methoxypyridine, and 4-pyridinemethanol.

Particularly useful tertiary amines subject to quaternization comprise N,N-dimethylalkanol amines such as 3-hydroxypropyl dimethylamine and 2-dimethylamino-1-ethanol. Other preferred tertiary amines include n-butyl dimethylamine, and N,N-dimethylbenzylamine, 4-ethylpyridine, and 1-methylimidazole, 1-benzylimidazole, N-methylmorpholine, and particularly 2-[2-(dimethylamino)ethoxy]ethanol.

In addition to quaternized epihalohydrin and unquaternized epihalohydrin, the backbone of the quaternized poly (epihalohydrin) polymer ("QPEHH" or "QPECH" where the epihalohydrin is epichlorohydrin) may optionally include repeating units that are residues of alkylene oxides such as ethylene oxide, propylene oxide, butylene oxide, 3,4-epoxy-1-butanol, 2,3-epoxy-1-propanol, or glycidol. Polymers of this structure may be prepared by co-polymerizing one or more alkylene oxides and epihalohydrin, followed by quaternization of epihalohydrin repeating units. The distribution of epihalohydrin units and alkylene oxide units in the backbone may be random, block, or other pattern. Where plural alkylene oxides are used in the polymerization, the backbone comprises repeating units that are residues of more than one alkylene oxide.

For convenience and familiarity of nomenclature, the description of the electrodeposition composition and method hereinafter will refer to "QPECH" levelers. However, it will be understood that, unless otherwise stated, the description encompasses polymers derived from other epihalohydrins, including principally epibromohydrin. The use of epichlorohydrin is highly preferred.

Where the number of alkylene oxide units in the QPECH backbone is q, the ratio of q/n+p+q is preferably not greater than 0.05 in those embodiments where the properties provided by presence of alkylene oxide repeat units is not needed; and typically between about 0.05 and about 0.50, more typically between about 0.10 and about 0.40 where their presence is warranted. In certain preferred embodiments, q is essentially zero and the QPECH consists essentially of repeating units that are residues of epihalohydrin and repeating units that are residues of quaternized epihalohydrin. In such embodiments, the poly(epihalohydrin) may be depicted by the structure:

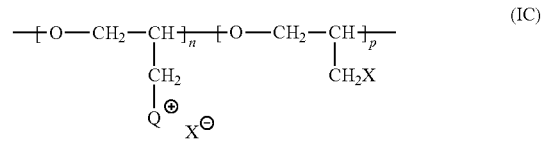

where Q is as described above.

Regardless of the presence or absence of alkylene oxide repeat units and regardless of the value of q, the ratio of n/n+p can have a bearing on the relative efficacy of the leveler. In certain embodiments, where there are polar substituents on the quaternized tertiary amine, e.g., 3-hydroxypropyl dimethylamine, the ratio of n/n+p is preferably at least 0.40 and more preferably between about 0.40 and about 0.60. These preferences may also apply where the quaternized tertiary amine contains aryl or aralkyl groups. In other embodiments wherein the tertiary amine is more hydrophobic, for example, n-butyl dimethylamine, the value of n/n+p is preferably at least about 0.70, more preferably, between about 0.70 and 1.0, more preferably at least about 0.75, still more preferably at least about 0.80, e.g., between about 0.80 and about 0.95, and most preferably in the range of about 0.90.

Where the poly(epichlorohydrin) contains alkylene oxide units, and there are polar substituent on the quaternary nitrogen. and q/n+p+q is at least about 0.05, n/n+p+q is preferably at least about 0.20, or between about 0.40 and about 0.60. Where the substituents on the quaternary nitrogen are hydrophobic e.g., where they are all hydrocarbyl groups, n/n+p+q is preferably between about 0.60 and about 0.95, more preferably between about 0.70 and about 0.9, most preferably between about 0.75 and about 0.90.

Regardless of whether the repeating units include alkylene oxide residues, the chain of repeating units of the polymer may optionally be bonded to a residual oxygen of an alcohol. For example, plural QPECH chains can be bonded to residual oxygens of a monomeric polyol as described in U.S. Pat. Pub. No. 2006/0062753 to Naraghi, the subject matter of which is herein incorporated by reference in its entirety. The preparation of such compositions comprises the polymerization of epihalohydrin and the condensation of the polymer with the hydroxyl groups of glycerin, as catalyzed, for example, by boron trifluoride. Once the PECH/polyol adduct is formed, epihalohydrin repeating units can be quaternized with an appropriate tertiary amine.

Average molecular weight of the QPECH may vary significantly depending, for example, on the molecular weight of the amine to be quaternized, the fraction of repeating units that comprise quaternary ammonium groups, and the extent to which the polymer backbone comprises repeating units derived from a co-monomer such as an alkylene oxide. These structural features are combined to enhance the polarization imparted by the QPECH while preserving compatibility of the compound with the electrolytic solution, thus achieving a favorable relationship between efficacy and solubility of the QPECH in the solution. Generally, solubility varies inversely with molecular weight while the extent of quaternization enhances solubility at a given molecular weight. The PECH with which the tertiary amine is reacted may have a weight average molecular weight that ranges, for example, between about 300 and about 4,000 but is preferably in the range of about 1,700 to about 2,200. After reaction of the PECH or ECH/alkylene oxide copolymer with the tertiary amine, the weight average molecular weight of the quaternized polymer may typically range from about 500 to about 10,000, or even higher depending on the overall structure of the QPECH and the overall composition of the electrodeposition bath, more preferably between about 800 and about 6,000, or between about 1,200 and about 3,000, or still more preferably between about 2,500 and about 4,000.

Advantageously, the synthesis of the QPECH can be integrated into the formulation of the electrodeposition composition. Conventionally, a QPECH is formed by condensation of pendent methylene halide groups of poly(epihalohydrin) with a tertiary amine in an aqueous medium. Because the temperatures required for the quaternizing reaction are relatively high, in excess of about 95° C., for example in the range of about 95° to about 100° C., quaternization in an aqueous medium requires the reaction to be conducted in a pressure vessel and the reaction mass cooled before it is removed from the reactor, thereby limiting productivity and/or requiring a high pressure heat exchanger to cool any of the reaction mass that may be removed immediately after the reaction.

In the integrated process for formulating the electrodeposition bath, the quaternization reaction is conducted in a medium comprising a relatively high boiling polar organic solvent, preferably having a boiling point of at least about 120° C., for example, between about 120° and about 220° C., more preferably between about 160° and about 200° C. The use of a high boiling solvent allows the reaction to be conducted at high temperature but ambient pressure, the reaction mass to be removed from the reactor immediately on completion of the reaction cycle, and the reaction mass to be cooled by flow of heat transfer fluid through coils in an atmospheric reaction vessel, or in withdrawal from the reactor through an external heat exchanger which need be pressurized only to the extent incident to fluid flow.

A solution of poly(epihalohydrin) in the polar solvent is initially prepared having a PECH concentration that may typically fall in the range between about 10 and about 35 percent by weight. A tertiary amine is added in a proportion governed by the extent of quaternization that is to be achieved. The quaternization reaction proceeds at a temperature that is normally in the range of about 160° to about 190° C.

Exemplary polar solvents for the quaternization include, for example, ethylene glycol, propylene glycol, glycerin, ethylene glycol monomethyl ether, ethylene glycol monoethyl ether, ethylene glycol monopropyl ether, and dipropylene glycol monomethyl ether. In a batch reaction system, the reaction cycle is generally between about 0.5 and about 3 hours.

Where polyol/QPECH adducts having the structure of those described in U.S. Pat. Pub. No. 2006/0062753 to Naraghi are prepared, epihalohydrin may be polymerized in the presence of a polyol and, typically, a polymerization catalyst such as BF3. The resulting adduct of polyol and PECH is then reacted with a tertiary amine in a polar solvent medium. Where epihalohydrin is polymerized in the presence of a sufficient excess of polyol, unreacted polyol may optionally function thereafter as the solvent for the subsequent quaternization reaction.

Once the reaction is complete and the quaternization reaction mass has been cooled, the reaction mass can be directly combined in an aqueous electrolytic plating bath with the copper salt, suppressor, chloride ion. Optionally, depending on the size and geometry of the base structure, an accelerator may also be included. It is not necessary to recover the QPECH from the quaternization reaction medium. In these embodiments, the plating composition contains the polar organic solvent, typically in a concentration between about 5 and about 50 mg/l. The ratio of leveler to polar organic solvent in the electrodeposition solution is typically between about 0.2:1 to about 1.5:1, more typically about 1:1.

In other embodiments of the process, a polar solvent is not necessarily present. For example, if the QPECH is acquired in neat form from an independent source, there may be no need or occasion for the presence of a polar solvent in the electrolytic plating bath.

Preferably, the electrodeposition composition also contains a suppressor. The suppressor component may be a conventional nonionic polyoxyalkylene polymer such as, for example, polyethylene glycol, polypropylene glycol, a block copolymer of ethylene oxide and propylene oxide, an alkoxylated alcohol comprising a polyether substituent comprising polyethylene oxide, polypropylene oxide, or a copolymer of ethylene oxide and propylene oxide, for example, as disclosed in U.S. Pat. Pub. No. 2002/0043467 to Morrissey, the subject matter of which is herein incorporated by reference in its entirety, or a cationic alkoxylated amine suppressor such as disclosed in U.S. Pat. No. 7,303,992 to Paneccasio et al., the subject matter of which is also herein incorporated by reference in its entirety.

Particularly preferred suppressors for the electrodeposition compositions used in the process described herein comprise polyether groups covalently bonded to a cationic species. The cationic polyether suppressor preferably comprises a nitrogen atom. Exemplary cationic species comprising a nitrogen atom include primary, secondary, tertiary, and quaternary amines. By "cationic," what is meant is that the polyether suppressor either contains or can contain a positive charge in solution. Primary, secondary, and tertiary amines are weakly basic and become protonated and positively charged when added to a solution comprising an acid. Quaternary amines comprise four nitrogen-substituents, and a quaternized nitrogen possesses a positive charge regardless of the solution pH. The primary, secondary, tertiary, and quaternary amines can be substituted or unsubstituted alkyl amines, substituted or unsubstituted cycloalkyl amines, substituted or unsubstituted aromatic amines, substituted or unsubstituted heteroaryl amines, substituted or unsubstituted alkylether amines, and substituted or unsubstituted aromatic alkyl amines.

The suppressors comprising polyether groups covalently bonded to a cationic species preferably comprise at least one amine functional group, preferably between two amine functional groups and five amine functional groups. Accordingly, the cationic species can be an amine, a diamine, a triamine, a tetraamine, a pentamine, or an even higher amine. The alkyl group of the alkylamine can be a substituted or unsubstituted alkyl, preferably a short chain hydrocarbon having between 1 and 8 carbons, which may be branched or straight chained. Exemplary alkylamines include, for example, methylamine, ethylamine, propylamine, n-butylamine, isobutylamine, t-butylamine, ethylenediamine, diethylenetriamine, 1,3-diaminopropane, 1,4-diaminobutane, 2-butene-1,4-diamine, and others, such as, for example, alkoxylated diethylene triamine or alkoxylated triethylene tetramine wherein poly(oxyalkylene) polyether groups are covalently bonded to a cationic nitrogen, and are preferably prepared by reaction of alkylene oxides with the oligo(alklene imine) substrate whose residue constitutes the core amine structure of the suppressor. The cycloalkyl group of the cycloalkyl amine typically comprises a 5- or 6-carbon ring, although bicyclic, tricyclic, and higher multi-cyclic alkyl amines are usable in the present invention. Exemplary cycloalkyl amines include, for example, substituted or unsubstituted cyclopentylamines, cyclohexylamines, cyclopentylamines, cyclopentyldiamines, cyclohexyldiamines, cyclopentylamines, cylcoalkyltriamines, and higher cycloalkyl amines. Alkylether amines preferably comprise an ether moiety defined by short chain hydrocarbons typically having between 1 and 8 carbons, such as diethylene glycol diamine and triethylene glycol diamine.

In one embodiment, the polyethers comprise a chain of repeat units, wherein the chain of repeat units can be formed by the polymerization of epoxide monomers. Most preferably, the suppressor comprises a cationic species in which the polyether chain is bonded directly to the nitrogen of an amine or other nitrogen-containing species. In a preferred embodiment, the epoxide monomers are selected from ethylene oxide monomer, propylene oxide monomer, and a combination thereof. Preferably, the polyether comprises a chain of repeat units formed by the polymerization of both ethylene oxide monomer and propylene oxide monomer. Accordingly, the ratio of ethylene oxide (EO) repeat units and propylene oxide (PO) repeat units in the polyether can be between about 1:9 and about 9:1. In especially preferred embodiments, the ratio is between about 2:3 and about 2:1, more preferably about 3:2. In certain preferred embodiments, the polyether comprises between about 1 and about 30 EO repeat units and between about 30 and about 1 PO repeat units, such as between about 7 and about 15 EO repeat units and between about 15 and about 7 PO repeat units. In one embodiment, the polyether comprises, for example, about 11 EO repeat units and about 13 PO repeat units. In other preferred embodiments, the polyether comprises about 7 or 8 EO repeat units and about 9 PO repeat units. Accordingly, the molecular weight of the polyether can be between about 100 g/mol and about 20,000 g/mol, more preferably between about 3500 and about 15,000 g/mol, more preferably between about 6000 and about 8000 g/mol.

The polyether preferably comprises EO repeat units and PO repeat units in random, alternating, or block configurations. In a random configuration, the EO repeat units and PO repeat units have no discernable linear pattern along the polyether chain. In an alternating configuration, the EO repeat units and PO repeat units alternate according to some defined pattern, such as repeating units of EO-PO, PO-EO, and other alternating patterns. The copolymer can be arranged in a block configuration. In the block configuration, the linear portion of the polyether chain comprises a block of EO repeat units bonded to a block of PO repeat units. The polyether chain may comprise a diblock. That is, the chain may comprise a first block of EO repeat units bonded to a second block of PO repeat units. Alternatively, the chain may comprise a first block of PO repeat units bonded to a second block of EO repeat units. In more complicated block configurations, the polyether chain may comprise a triblock (EO block-PO block-EO block or PO block-EO block-PO block), tetrablock, pentablock, or higher block arrangements. It has been discovered that a PO block-EO block-PO triblock configuration is effective to reduce polyether suppressor foaming in electrolytic solution. In one embodiment of the block configuration, each block of repeat units comprises between about 1 and about 30 repeat units, more preferably between about 7 and about 15 repeat units. In a preferred embodiment involving a PO block-EO block-PO block tri-block configuration, the first PO-block bonded to the cationic species comprises between about 7 and about 15 PO repeat units, the second EO-block bonded to the PO-block comprises between about 7 and about 15 repeat units, and the third PO-block bonded to the second EO-block comprises between about 1 and about 5 repeat units.

Optionally, the PO/EO polyethers are capped by a substituted or unsubstituted alkyl group, aryl group, aralkyl, or heteroaryl group. A preferred capping moiety for its ease of manufacture and low cost is a methyl group.

The suppressor compounds comprising polyether groups covalently bonded to a cationic species comprise a positive charge in acidic solution and repeat units, EO and PO. It is thought that the separate functionalities of the positive charge, the EO repeat units, and the PO repeat units contribute different chemical and physical properties which affect, and thereby enhance, the function of the polyether as a suppressor in copper plating compositions useful in the electrodeposition process.

Without being bound to a particular theory, it is thought that the positive charge of the cationic species enhances the attraction of the suppressor compound to copper deposited into interconnect features, which, during an electrolytic plating operation, functions as the cathode. It is believed that the PO repeat unit is the active repeat unit in the suppressors that are useful in the electrodeposition process. That is, the PO repeat unit has suppressor functionality and affects the quality of the copper deposit. Without being bound to a particular theory, it is thought that the PO repeat units, being relatively hydrophobic form a polarizing film over a copper seed layer and electrolytically deposited copper.

Where the polyether substituent is a block copolymer of PO and EO, it is particularly preferred that a PO block is bonded to a nitrogen of an amine or other nitrogen-containing species. The combination of the positively charged nitrogen atom and the hydrophobic PO block enhances the affinity of the suppressor for the cathodic copper substrate. This is believed to enhance the suppressive effect of the alkoxylated amine suppressor. An especially effective suppressor comprises a hexaalkoxylated triethylene tetraamine as follows:

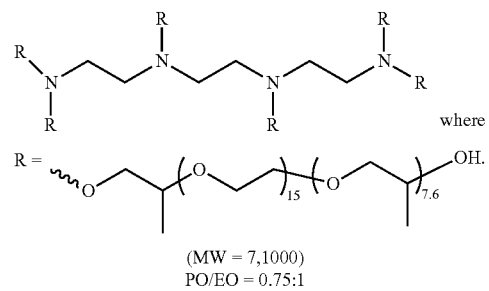

(MW = 7,1000)
PO/EO = 0.75:1

Another similar suppressor contains:

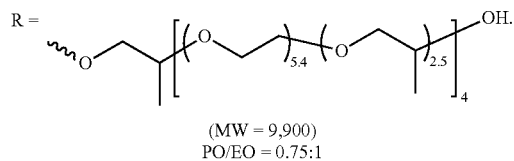

(MW = 9,900)
PO/EO = 0.75:1

Another suppressor of interest is the following triamine:

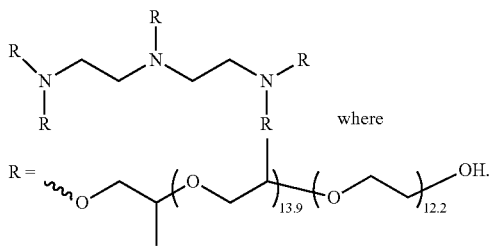

where

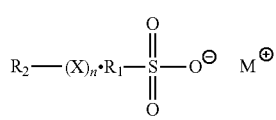

Preferably, the electrodeposition composition contains the between about 100 and about 1,000 mg/L, more preferably between about 200 and about 600 mg/L suppressor.

The electrodeposition composition also preferably contains an accelerator. The accelerator may include an organic sulfur compound. Preferred organic sulfur compounds include water soluble organic divalent sulfur compounds. In one embodiment, the organic sulfur compound has the following general structure (11):

Structure (11)

$$R_2-(X)_n\cdot R_1-\overset{\overset{O}{\|}}{\underset{\underset{O}{\|}}{S}}-O^\ominus \quad M^\oplus$$

wherein
X is O or S, preferably S;
n is 1 to 6;
M is hydrogen, alkali metal, or ammonium as needed to satisfy the valence;
$R_1$ is an alkylene or cyclic alkylene group of 1 to 8 carbon atoms, an aromatic hydrocarbon or an aliphatic aromatic hydrocarbon of 6 to 12 carbon atoms; and
$R_2$ is selected from the group of $MO_3SR_1$ wherein M and $R_1$ are as defined above,
a thiocarbamate represented by the formula:

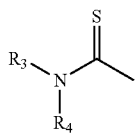

a xanthate represented by the formula:

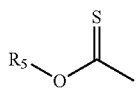

and an aminoimine represented by the formula:

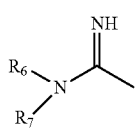

wherein $R_3$, $R_4$, $R_5$, $R_6$, and $R_7$ are independently hydrogen, an alkyl group of 1 to 4 carbon atoms, a heterocyclic group, or an aromatic group. In one preferred embodiment, X is Sulfur, and n is two.

A preferred organic sulfur compound of Structure (1) has the following general structure (12):

Structure (2)

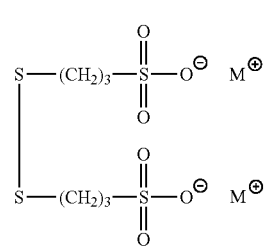

wherein M is a counter ion possessing charge sufficient to balance the negative charges on the oxygen atoms. M may be, for example, protons, alkali metal ions such as sodium and potassium, or another charge balancing cation such as ammonium or a quaternary amine.

One example of the organic sulfur compound of structure (2) is the sodium salt of 3,3' dithiobis(1-propanesulfonate), which has the following structure (13):

Structure (3)

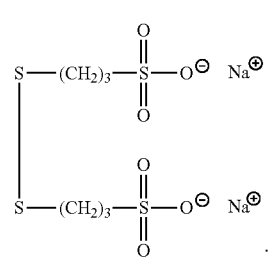

An especially preferred example of the organic sulfur compound of structure (2) is 3,3'-dithiobis(1-propanesulfonic acid), which has the following structure (14):

Structure (4)

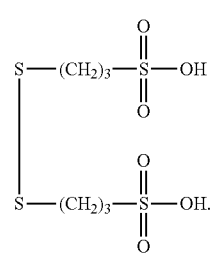

Another preferred organic sulfur compound of Structure (1) has the following general structure (5):

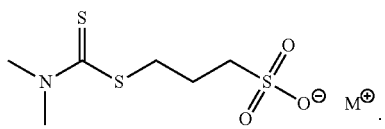

Structure (5)

One example of the organic sulfur compound of structure (16) is 3-(dimethylcarbamothioylthio)propane-1-sulfonic acid:

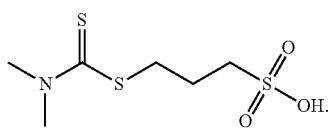

Structure (16)

Another suitable sulfur compound comprises the following structure:

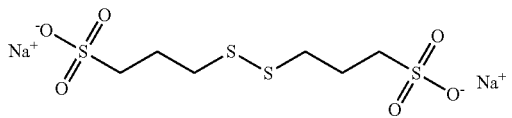

The organic sulfur compound may be added in a concentration between about 1 mg/L and about 100 mg/L (ppm), such as between about 25 mg/L and 70 mg/L.

In other embodiments, the accelerator may be an oxidized version of one of the foregoing accelerator compounds.

The process described herein is useful for building copper bumps and pillars in flip chip packaging and for other wafer-level packaging features such as through silicon vias and redistribution layers (RDLs) and processes directed to the manufacture of integrated circuits. In wafer level packaging, an array of copper bumps or pillars is provided over a semiconductor substrate for interconnection of an electric circuit of a semiconductor device with a circuit external to the device, for example, to a printed circuit board (PCB) or another integrated chip circuit. Current is supplied to the electrolytic solution while the solution is in contact with a cathode comprising an under bump structure on a semiconductor assembly. The semiconductor assembly comprises a base structure bearing the under bump structure, and the latter comprises a seminal conductive layer that may comprise either under bump metal, which is preferably copper or a copper alloy, or an under bump pad that comprises another conductive material such as, for example, a conductive polymer. An under bump metal structure may comprise, for example, a copper seed layer as provided by physical vapor deposition.

In the electrodeposition of pillars, and optionally also in the deposition of bumps, the under bump structure is positioned within or extends into a concavity in the surface of the base structure. The configuration of said bump or pillar is defined by the complementary configuration of the concavity.

In one embodiment, the concavity comprises a floor comprising the under bump pad or under bump metal and a sidewall comprising a dielectric material. In another embodiment, the base structure comprises a dielectric layer comprising a photoresist, mask, or stress buffer material and the concavity comprises an opening in a surface of the dielectric layer. In this instance, the dielectric layer may be removed after electrodeposition of said bump or pillar.

In addition, the sidewall of the concavity can be provided with a dielectric liner prior to electrodeposition of the bump or pillar. In other words, the cavity in which copper is to be deposited may first be provided with a dielectric liner such as silicon dioxide or silicon nitride. The dielectric liner can be formed, for example, by chemical vapor deposition or plasma vapor deposition. Alternatively, organic dielectrics can be used to mitigate a coefficient of thermal expansion mismatch. A photoresist wall of the cavity may have sufficient dielectric properties to obviate the need for a further dielectric layer. However, the nature of the vapor deposition process may cause a further dielectric layer to form on the photoresist wall as well. A seminal conductive layer is then provided by either chemical vapor deposition of a seed layer.

In a process for forming bumps and pillars, the conductive under bump structure may be deposited only at the bottom, i.e., the floor, of the cavity, or in some embodiments, such as those illustrated and described in U.S. Pat. No. 8,546,254 to Lu et al., the subject matter of which is herein incorporated by reference in its entirety, the conductive under bump structure may extend from the bottom of the concavity for some distance upwardly along the sidewall. Preferably, at least the upper sidewall of the concavity remains non-conductive. The bottom of the concavity can be flat, or may comprise a recess filled with polyimide that promotes better bonding. This embodiment of the process differs from filling TSVs, for example, in which the seminal conductive layer is formed over the entire surface of the cavity, including bottom and sidewalls, and metallization is carried out to deposit copper on both bottom and sidewalls.

In carrying out the process described herein, current is supplied to an electrolytic circuit comprising a direct current power source, the aqueous electrodeposition composition, an under bump pad, under bump metal, or array of under bump pads or metal in electrical communication with the negative terminal of the power source and in contact with the electrodeposition composition, and an anode in electrical communication with the positive terminal of the power source and in contact with the electrodeposition composition.

In wafer level packaging, under bump structures are arrayed on a face of a semiconductor wafer, the under bump structure is electrically connected to the negative terminal of the power source, the semiconductor wafer and anode are immersed in the electrodeposition bath, and the power applied. Using the electrodeposition composition described herein within wafer (WIW) uniformity is maintained at a standard deviation not greater than about 10%, for example, while within die (WID) uniformity for dies cut from the wafer is maintained at a standard deviation of, for example, not greater than about 10%. Average feature (WIF) doming is typically about 10%, for example, for baths containing a single leveler. However, greater deviation may be tolerated in situations where productivity gains can be achieved or the device has greater tolerance of the deviation can be remedied downstream by, for example, a mechanical copper removal process. Doming and dishing of bumps and pillars can be minimized, and relatively flat head bumps and pillars can be prepared, using electrodeposition baths containing combinations of levelers as described herein.

The process can be used to provide the under bump metal pads for flip chip manufacturing in which case the metalizing substrate is generally limited to the faces of the bonding pads. Alternatively, with reference to the under bump metal as the floor, the process can be used to form a copper bump or pillar by bottom-up filling of the cavity formed at its floor by the under bump pad or under bump metal and on its sides by the sidewall of an opening in a stress buffer layer and/or photoresist that allows access to the pad or under bump metal. In the latter application, the aperture size of the cavity is roughly comparable to that of a blind through silicon via, and the parameters of the process for building the bump or pillar are similar to those used for filling blind TSVs. However, the concavity wall provided by openings in photoresist or stress-reducing material is ordinarily not seeded and is therefore non-conductive. Only a semiconductor or dielectric under bump structure at the floor of the cavity is provided with a seminal conductive layer, typically comprising a conductive polymer such as a polyimide. In such embodiments, the process is not as dependent on the balance of accelerator and suppressor as it is in the case of bottom filling submicron vias or TSVs.

During the electrodeposition of a bump or pillar within a concavity in the surface of the base structure, lateral growth thereof is constrained by the sidewall(s) of the concavity, and the configuration of the bump or pillar is defined by the complementary configuration of the concavity.

In other embodiments, a bump may be grown over the under bump metal or pad without lateral constraint, or may be caused to grow above the upper rim of a concavity or other lateral constraint, in which case a bump is formed that typically assumes a generally spherical configuration. However, in these embodiments, the configuration of the bump can be influenced by the orientation, configuration and dimension of the anode in the electrolytic circuit.

As described, for example, in U.S. Pat. No. 8,546,254 to Lu et al., the subject matter of which is herein incorporated by reference in its entirety, an anode immersed in an electrodeposition bath can be brought into registry with an under bump structure that is also immersed in the bath, or each of an array of anodes can be brought into registry with a complementary array of under bump structures within the bath, and current applied to deposit a bump or pillar on the under bump structure. If growth of the bump is not constrained by the sidewall of a concavity, or if application of current is continued to a point that the growing bump extends outside the concavity or other lateral constraint, growth of the distal end of the bump assumes a spherical or hemispherical shape as illustrated in FIG. 2B of the '254 patent. As further described therein, the anode may be pulled away from the substrate along the axis of the growing bump, and the vertical rate of withdrawal of the anode from substrate can affect the shape of distal end of the bump. Generally, the faster the pulling rate, the higher the tangential angle θ (theta) between a horizontal plane and the growing bump at any given distance between the location of the plane and the under bump metal or pad. As further described in the '254 patent, the pulling rate is not necessarily constant but, if desired, can be varied with deposition time or extent of vertical growth. Alternatively, the under bump structure can be pulled away from the anode instead of the anode being pulled away from substrate. In addition to the pulling rate of the anode, the voltage difference between the anode and the cathode (initially the under bump structure and thereafter the growing bump) can also affect the shape of the bump.

The inventors of the present invention have found that, where a solder bump is added at the distal end of a copper bump or pillar that has been formed by the process described herein, the solder bump adheres seamlessly to the copper with a minimum of Kirkendall voids. Thus a solder bump comprised of a low melting alloy such as, for example, Sn/Ag or Sn/Pb, can be directly applied to the copper pillar or bump without need for a cap on the copper containing an intermediate layer of nickel or Ni alloy. Also Kirkendall voids are substantially avoided at the juncture between the copper bump or pillar and an under bump metal.

It has also been shown that the use of the compositions described herein provides a high level of within die (WID) and within wafer (WIW) uniformity in the deposition of arrays of copper bumps or pillars on a wafer that has been provided with an array of under bump structures as also described herein.

Using the levelers described herein, high current densities can be established and maintained throughout the electrodeposition process. Thus, the rate at which a bump or pillar may be caused to grow in the vertical direction is at least about 0.25 μm/min, more typically at least about 2.5 or about 3 μm/min, and even more typically at least about 3.3 μm/min. Achievable growth rates range up to about 10 μm/min or higher, equating to a current density of at least about 1 A/dm$^2$, at least about 12 A/dm$^2$, or at least about 20 A/dm$^2$, ranging up to about 30 A/dm$^2$ or higher.

Although polymeric and oligomeric reaction products of dipyridyl and a difunctional alkylating agent are highly effective for promoting the deposition of copper bumps and pillars that are free of Kirkendall voids, and for achieving favorable WID, WIW and within feature (WIF) metrics, there is a tendency for pillars produced from the baths described herein to have substantial doming, except in the case of N-benzyl substituted polyethylene imine, wherein the distal end of a bump or pillar is more typically dished.

While the foregoing discussion of the invention is directed primarily to embodiments involving bumps and pillars, the compositions and methods have also been proven to be effective in forming other WLP copper features including megabumps, through silicon vias, and redistribution layers. The compositions and processes also apply to heterogeneous WLPs and semiconductor substrates other than Si-based substrates, such as, for example, GaAs-based substrates.

The invention is further illustrated by the following non-limiting working examples.

Example 1

Mega Pillar Aspect Ratio ~1:1, plate speed 3-7 μm/min, and feature size 240 μm(w)×210 μm(h).

One exemplary preferred electrodeposition composition contains between about 28 and about 35 g/L copper ions in the form of copper sulfate or copper methane sulfonate, between about 150 and about 200 g/L sulfuric acid or methane sulfonic acid, between about 40 and about 50 mg/L SPS, between about 200 and 400 mg/L hexaalkoxylated triethylene tetramine and between 12 and about 15 mg/L leveler of structure IV, VI, VII, VIII, VIA, VIIIA, XXX or combinations of such structures. The weight ratio of hexaalkoxylated triethylene tetramine to leveler dipyridyl polymer is preferably between about 10:1 and about 40:1, more preferably between about 14:1 and about 20:1.

Example 2

Mega Pillar Aspect Ratio ~4:1, plate speed 3-7 μm/min, and feature size 60 μm(w)×220 μm(h).

Another exemplary preferred electrodeposition composition contains between about 55 and about 65 g/L copper ions in the form of copper sulfate or copper methane sulfonate, between about 80 and about 120 g/L sulfuric acid or methane sulfonic acid, between about 40 and about 60 mg/L SPS accelerator, between about 200 and 400 mg/L hexaalkoxylated triethylene tetramine suppressor and between 12 and about 15 mg/L of leveler of structure IV, VI, VII, VIII, VIA, VIIIA, XXX or combinations of such structures. The weight ratio of hexaalkoxylated triethylene tetramine to dipyridyl polymer is preferably between about 10:1 and about 40:1, more preferably between about 14:1 and about 20:1.

Example 3

Mega Pillar Aspect Ratio ~1.5:1 plate speed 3-7 μm/min, and feature size 150 μm(w)×220 μm(h).

Yet another exemplary preferred electrodeposition composition contains between about 55 and about 65 g/L copper ions in the form of copper sulfate or copper methane sulfonate, between about 80 and about 120 g/L sulfuric acid or methane sulfonic acid, between about 10 and about 30 mg/L SPS, between about 500 and 700 mg/L hexaalkoxylated triethylene tetramine suppressor and between 3 and about 8 mg/L of leveler of structure IV, VI, VII, VIII, VIA, VIIIA, XXX or combinations of such structures. The weight ratio of hexaalkoxylated triethylene tetramine to dipyridyl polymer is preferably between about 50:1 and about 250:1, more preferably between about 110:1 and about 170:1.

Example 4

Redistribution layer with Aspect Ratio ~1:1, plate speed 0.5-2 μm/min, and feature size 2 μm(w)×2 μm(h).

An additional exemplary preferred electrodeposition composition contains between about 25 and about 35 g/L copper ions in the form of copper sulfate or copper methane sulfonate, between about 170 and about 220 g/L sulfuric acid or methane sulfonic acid, between about 45 and about 55 mg/L SPS, between about 200 and 400 mg/L hexaalkoxylated triethylene tetramine and between 3 and about 6 mg/L of leveler of structure IV, VI, VII, VIII, VIA, VIIIA, XXX or combinations of such structures. The weight ratio of hexaalkoxylated triethylene tetramine to dipyridyl polymer is preferably between about 40:1 and about 90:1, more preferably between about 50:1 and about 70:1.

Example 5

TSV+RDL (2in1) Aspect Ratio ~1:1, plate speed 0.1-1 μm/min, and feature size 2 μm(w)×2 μm(h) to 100 μm (h).

Yet another exemplary preferred electrodeposition composition contains between about 40 and about 60 g/L copper ions in the form of copper sulfate or copper methane sulfonate, between about 80 and about 120 g/L sulfuric acid or methane sulfonic acid, between about 1 and about 10 mg/L SPS, between about 10 and 100 mg/L ethoxylated and propoxylated butanol and between 1 and about 10 mg/L of leveler of structure IV, VI, VII, VIII, VIA, VIIIA, XXX or combinations of such structures. The weight ratio of hexaalkoxylated triethylene tetramine to dipyridyl polymer is preferably between about 1:1 and about 100:1, more preferably between about 2:1 and about 50:1.

Example 6

Microbump/Pillar Aspect Ratio ~1-2:1, plate speed 1-2.5 μm/min, and feature size: 20-80 μm(w)×20-100 μm(h).

Yet another exemplary preferred electrodeposition composition contains between about 25 and about 55 g/L copper ions in the form of copper sulfate or copper methane sulfonate, between about 80 and about 200 g/L sulfuric acid or methane sulfonic acid, between about 75 and about 125 mg/L SPS, between about 200 and 600 mg/L hexaalkoxylated triethylene tetramine and between 8 and about 20 mg/L of leveler of structure IV, VI, VII, VIII, VIA, VIIIA, XXX or combinations of such structures. The weight ratio of hexaalkoxylated triethylene tetramine to dipyridyl polymer is preferably between about 10:1 and about 75:1, more preferably between about 30:1 and about 40:1.

Example 7

In order to able to better predict how certain combinations of levelers, suppressors and accelerators would work in plating copper features, a series of experiments were run in which different combinations of levelers, suppressors and accelerators were used. It is not yet understood while certain combinations provided a good result and other combinations provided a result that was not as successful.

Table 1 lists various levelers, suppressors and accelerators:

| Compound | Structure |
|---|---|
| Accelerator 1 | 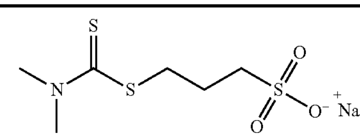 |
| Accelerator 2 | 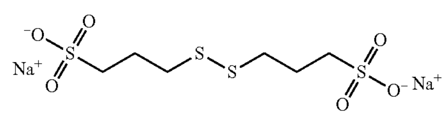 |
| Leveler 1 | 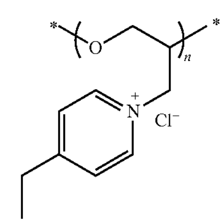 |
| Leveler 2 | where X is 0.3 to 0.7. |
| Suppressor 1 | 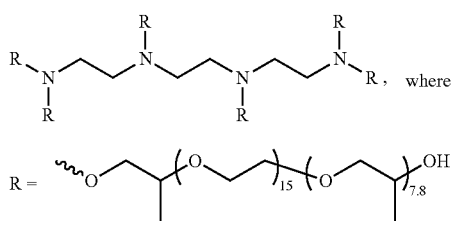 |

Table 1 lists various levelers, suppressors and accelerators:

| Compound | Structure |
|---|---|
| Suppressor 2 | 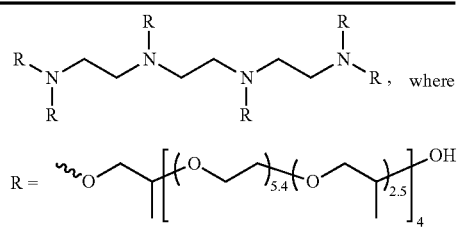 |

Table 2 provides the results of the various combinations of accelerators, levelers and suppressors of Table 1:

TABLE 2

| Run | Acc. mg/L | Leveler mg/L | Supp. mg/L | Ave. H μm | WID μm | WIF μm | Comments |
|---|---|---|---|---|---|---|---|
| 1 | Acc. 2 40-50 | Lev. 1 10-20 | Supp. 1 800-1200 | 196 | 25 | 8.1 | Need flatter, better fill |
| 2 | Acc. 1 40-50 | Lev. 1 10-20 | Supp. 1 800-1200 | 194 | 32 | 1.2 | Better TIR, need better BHR |
| 3 | Acc. 1 40-50 | Lev. 1 10-20 | Supp. 2 800-1200 | 205 | 31 | −10 | Dished is preferred to doming, need better BHR |
| 4 | Acc. 2 40-50 | Lev. 2 10-20 | Supp. 2 800-1200 | 217 | 23 | 1.2 | Best system, robust |

Ave. H = average height of plated bump
WIF = illustrates how much the bump domes.
Positive value is doming, negative is dishing, 0 is flat The results showed that while Run 1 initial produced the best result, switching from Accelerator 2 to Accelerator 1 (Run 2) greatly reduced the doming as the different accelerators performed differently with the same leveler (and same suppressor). In Run 3, when the suppressor was changed to Suppressor 2, the dishing was large and the WID was too high. By switching the accelerator back to Accelerator 2 and using Leveler 2 and Suppressor 2, it was possible to get both flat bumps WIF and good WID.

Thus, it can be seen that it is not easy to predict the combination of levelers, suppressors and accelerators that are needed to provide plated bumps having good average height (greater than about 190 nm, preferably greater than about 200 nm, more preferably greater than about 210 nm or even 215 nm), values of WID within an acceptable range (less than about 30, more preferably less than about 25), and an acceptable WIF (−5≤TIR≤5, more preferably −1.0≤TIR≤1.0).

In view of the above, it will be seen that the several objects of the invention are achieved and other advantageous results attained.

As various changes could be made in the above compositions and processes without departing from the scope of the invention, it is intended that all matter contained in the above description and shown in the accompanying drawings shall be interpreted as illustrative and not in a limiting sense.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements. As used herein, the term "about" refers to a measurable value such as a parameter, an amount, a temporal duration, and the like and is meant to include variations of +/−15% or less, preferably variations of +/−10% or less, more preferably variations of +/−5% or less, even more preferably variations of +/−1% or less, and still more preferably variations of +/−0.1% or less of and from the particularly recited value, in so far as such variations are appropriate to perform in the invention described herein. Furthermore, it is also to be understood that the value to which the modifier "about" refers is itself specifically disclosed herein.

What is claimed is:

1. An electrodeposition composition comprising:
   a) a source of copper ions;
   b) an acid;
   c) a suppressor;
   d) a leveler, wherein the leveler comprises:
      (i) a quaternized dipyridyl compound, wherein the quaternized dipyridyl compound comprises a compound having a structure of a reaction product of N,N'-tetraalkylthiourea with an intermediate produced by a reaction of a dipyridyl with a difunctional alkylating agent; or
      (ii) a quaternized poly(epihalohydrin), wherein the quaternized poly(epihalohydrin) compound comprises n repeating units corresponding to structure 1N and p repeating units corresponding to structure 1P:

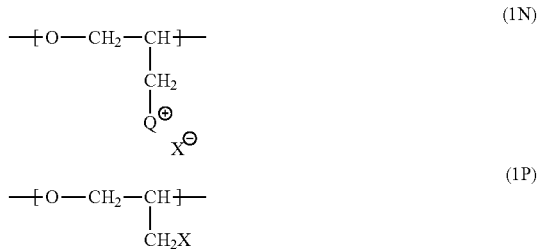

wherein Q has a structure corresponding to that which may be obtained by reacting a pendant methylene halide group of poly(epihalohydrin) with a tertiary amine selected from the group consisting of: (i) an N-substituted and optionally further substituted heteroalicyclic amine wherein the N-substituent is selected from the group consisting of substituted or unsubstituted alkyl, alicyclic, aralkyl, aryl, and heterocyclic and (ii) a substituted or unsubstituted nitrogen-containing heteroaryl compound; and
   wherein n is an integer between 3 and 35, p is an integer greater than 0 and up to 25, X is a halo constituent, and X is monovalent anion; and
   e) an accelerator.

2. The composition of any of claim 1, wherein the difunctional alkylating agent is selected from the group consisting of 1-chloro-2-(2-chloroethoxy)ethane, 1,2-bis(2-chloroethoxy)ethane, 1,3-dichloropropan-2-one, 1,3-dichloropropan-2-ol, 1,2-dichloroethane, 1,3-dichloropropane, 1,4-dichlorobutane, 1,5-dichloropentane, 1,6-dichlorohexane, 1,7-dichloroheptane, 1,8-dichlorooctane, 1,2-di(2-chloroethyl)ether.

3. The composition of claim 1, wherein the value of n is between 10 and 15.

4. The composition as set forth in claim 1, wherein Q is selected from the group consisting of:

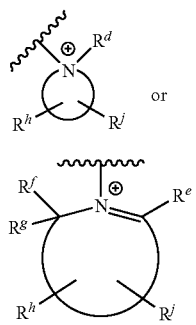

wherein: (i) structure IIB is an N-substituted heterocyclic moiety; (ii) structure IIC is a heterocyclic moiety; (iii) each of $R^a$, $R^b$, $R^c$ and $R^d$ is independently selected from the group consisting of substituted or unsubstituted alkyl, substituted or unsubstituted alkenyl, substituted or unsubstituted alkynyl, substituted or unsubstituted aralkyl, substituted or unsubstituted alicyclic, substituted or unsubstituted aryl, and substituted or unsubstituted heterocyclic; and (iv) each of $R^e$, $R^f$, $R^g$, $R^h$ and $R^j$ is independently selected from the group consisting of hydrogen, substituted or unsubstituted alkyl, substituted or unsubstituted alkenyl, substituted or unsubstituted alkynyl, substituted or unsubstituted aralkyl, substituted or unsubstituted alicyclic, and substituted or unsubstituted aryl, and substituted or unsubstituted heterocyclic.

5. The composition as set forth in claim 4, wherein the quaternized poly(epihalohydrin) comprises additional repeating units comprising residues of at least one alkylene oxide, or
   wherein the quaternized poly(epihalohydrin) comprises repeating units that are residues of ethylene oxide, or
   wherein the quaternized poly(epihalohydrin) comprises repeating units that are residues of propylene oxide.

6. The composition as set forth in claim 5, wherein the total of alkylene oxide repeating units in said quaternized poly(epihalohydrin) is q, and the ratio of q/n+p+q is not greater than about 0.05, or is between about 0.05 and about 0.50.

7. The composition as set forth in claim 1, wherein repeating units of said poly(epihalohydrin) consist essentially of residues of epihalohydrin and residues of quaternized epihalohydrin

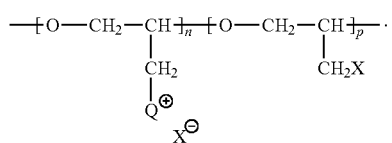

8. The composition as set forth in claim 1, wherein the quaternized poly(epihalohydrin) repeating units and non-quaternized epihalohydrin repeating units in said quaternized poly(epihalohydrin) are arranged in a block, alternating or random configuration.

9. The composition as set forth in claim 1, wherein Q has the structure which may be obtained from reacting a pendent methylene chloride group of poly(epihalohydrin) with a pendent methylene halide group with a tertiary amine selected from the group consisting of benzyldimethylamine, and 4-hydroxybenzyldimethyleamine, 2-methylpyridine, 3-methylpyridine, 4-methylpyridine, 2-ethylpyridine, 3-ethylpyridine, 4-ethylpyridine, 2-propylpyridine, 3-propylpyridine, 4-propylpyridine, 4-tetrabutylpyridine, 4-cyanopyridine, 4-isopropylpyridine, 4-methoxypyridine, 3,4-lutidine, 3-methoxypyridine, 4-methoxypyridine, 3-pyridinemethanol, and 4-pyridinemethanol.

10. The composition as set forth in claim 1, wherein the quaternized poly(epihalohydrin) comprises:

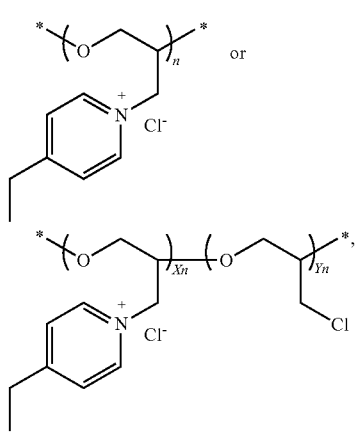

wherein X is between 0.3 and 0.7.

11. The composition as set forth in claim 1, wherein the aqueous electrodeposition composition further comprises an accelerator.

12. The composition as set forth in claim 11, wherein the accelerator comprises an organic sulfur compound having the following general structure (5):

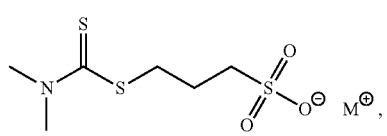

Structure (5)

wherein M is selected from the group consisting of alkali metal ions and charge balancing cations.

13. The composition as set forth in claim 1, wherein the suppressor comprises a compound selected from the group consisting of:
   a) an alkoxylated amine;
   b) a polyether compound comprising a combination of propylene oxide (PO) repeat units and ethylene oxide (EO) repeat units present in a PO:EO ratio between about 1:9 and about 9:1 and bonded to a nitrogen-containing species; and
   c) a polyalkylene glycol having a terminal sulfonic acid moiety and a terminal aromatic moiety formed by condensing a substituted phenol with a terminal hydroxyl of said polyalkylene glycol.

14. The composition as set forth in claim 13, wherein the suppressor is a polyether compound and the PO repeat units and EO repeat units are present in a PO:EO ratio between about 2:3 and about 2:1.

15. The composition as set forth in claim 13, wherein the suppressor is an alkoxylated amine, and the alkoxylated amine is selected from the group consisting of a tetraalkoxylated alkylene diamine, an alkoxylated diethylene triamine, a tetraalkoxylated triethylene tetraamine, and combinations of one or more of the foregoing.

16. The composition as set forth in claim 1, wherein the ratio of n/n+p is at least 0.4 and less than 1.0.

17. The composition as set forth in claim 16, wherein the ratio of n/n+p is between about 0.40 and about 0.60 or between about 0.70 and about 0.95.

\* \* \* \* \*